(12) United States Patent
Lorenz et al.

(10) Patent No.: US 6,258,855 B1
(45) Date of Patent: Jul. 10, 2001

(54) METHOD OF RETARDING AND AMELIORATING CARPAL TUNNEL SYNDROME

(75) Inventors: R. Todd Lorenz; Gerald R. Cysewski, both of Kailua-Kona, HI (US)

(73) Assignee: Cyanotech Corporation, Kailua-Kona, HI (US)

( * ) Notice: Subject to any disclaimer, the term of this patent is extended or adjusted under 35 U.S.C. 154(b) by 0 days.

(21) Appl. No.: 09/500,257

(22) Filed: Feb. 8, 2000

(51) Int. Cl.$^7$ .................................................. A61K 31/12
(52) U.S. Cl. ............................................................. 514/691
(58) Field of Search ............................................. 514/691

(56) References Cited

PUBLICATIONS

Goodman et al, "Effect of Local Corticosteroid Injection on Median Nerve Conduction in Carpal Tunnel Syndrome", Aug. 1962, 287–294.
Gelberman, M.D., et al, "Carpal–Tunnel Syndrome", Oct. 1980, 1181–1184.
Di Mascio et al, "Lycopene as the Most Efficient Biological Carotenoid Singlet Oxygen Quencher", Nov. 1, 1989, 532–538.
Bendich, Adrianne, "Carotenoids and the Immune Response", 1989, 112–115.
J. Terao, "Antioxidant Activity of B–Carotene–Related Carotenoids in Solution", 1989, 659–661.
Bendich, Adrianne, "Carotenoids and the Immune System", 1990, 323–335.
Kurashige et al, "Inhibition of Oxidative Injury of Biological Membranes by Astaxanthin", 1990, 27–38.
Miki, Wataru, "Biological Functions and Activities of Animal Carotenoids", 1991, 141–146.
Di Mascio et al, "Antioxidant defense systems; the role of carotenoid tocopherol and thiols", 1991, 194S–199S.
Jyonouchi et al, "Studies of Immunomodulating Actions of Carotenoids. I. Effects of B–Carotene and Astaxanthin on Murine Lymphocyte Functions and Cell Surface marker Expression in In Vitro Culture System", 1991, 93–105.
P. Bubrick, "Production of Astaxanthin from Haematococus", 1991, 237–239.
Suzuki et al, "Antioxidant activity of xanthophylss on peroxyl radical–mediated phospholipid peroxidation", 1992, 178–184.
Grung et al, "Algal Carotenoids 51. Secondary Carotenoids 2, Haematococcus pluvialis aplanospores as a source of astaxanthin esters" 1992, 165–171.
Palozza et al, "Astaxanthin and Canthaxanthin Are Potent Antioxidants in a Membrane Model", Sep. 1992, 291–295.
Witt et al, "Exercise, Oxidative Damage and Effects of Antioxidant Manipulation", 1992, 766–773.
Oshima et al, "Inhibitory Effect of B–Carotene and Astaxanthin on Photosensitized Oxidation of Phospholipid Bilayers", 1993, 607–615.
Jergensen et al, "Carotenoid scavenging of radicals", 1993, 423–429.
Jyonouchi et al, "Studies of Immunomodulating Actions of Carotenoids. II. Astaxanthin Enhances In Vitro Antibody Production to T–Dependent Antigents Without Facilitating Polyclonal B–Cell Activation", 1993, 269–280.
Tinkler et al, "Dietary carotenoid protect human cells from damage", 1994, 283–285.
Tjahjono et al, "Hyper–Accumulation of Astaxanthin In A Green Alga Haematococcus pluvialis At Elevated Temperatures", 1994, 133–138.
Jyonouchi et al, "Immunomodulating Actions of Carotenoids", 1994, 47–58.
Jyonouchi et al, "Astaxanthin, a Carotenoid without Vitamin A Activity, Augments Antibody Responses in Cultures Including T–helper Cell Clones and Suboptimal Doses of Antgent", 1995, 2483–2493.
Jyonouchi et al, "Effect of Carotenoids of In Vitro Immunoglobulin Production by Human Peripheral Blood Mononuclear Cells: Astaxanthin, a Carotenoid Without vitamin A Activity, Enhances In Vitro Immunoglobulin Production in Response to a T–Dependent Stimulant and Antigen", 1995, 171–183.
Li Li Ji, "Oxidative Stress During Exercise: Implication of Antioxidant Nutrients", 1995, 1079–1086.
Sen, Chandan, K., "Oxidants and antioxidants in exercise", 1995, 675–686.
Shimidzu et al, "Carotenoids as Singlet Oxygen Quenchers in Marine Organisms", 1996, 134–137.
Harker et al, "Factors Responsible for Astaxanthin Formation in the Chlorophyte Haematococcus pluvialis", 1996, 207–214.
Jyonouchi et al, "Effects of Various Carotenoids on Cloned, Effector–Stage T–Helper Cell Activity", 1996, 313–324.
Poulsen et al, "Extreme exercise and oxidative DNA modification", 1996, 343–346.
Dekkers et al, "The Role of Antioxidant Vitamins and Enzymes in the Prevention of Exercise–Induced Muscle Damage", 1996, 213–238.

(List continued on next page.)

Primary Examiner—Theodore J. Criares
Assistant Examiner—Jennifer M Kim
(74) Attorney, Agent, or Firm—Devine, Millimet & Branch, P.A.; Paul C. Remus; Kristin Kohler

(57) ABSTRACT

Astaxanthin is a potent antioxidant, over 500 times more powerful than Vitamin E and 10 times stronger than other carotenoids such as zeaxanthin, lutein, canthaxanthin and beta-carotene. Astaxanthin has also been shown to enhance and modulate the immune system. Disclosed is a method and treatment for retarding and ameliorating carpal tunnel syndrome (CTS) and tenosynovitis. The method comprises administering a source of astaxanthin in a therapeutically effective amount to prevent, retard and ameliorate carpal tunnel syndrome and tenosynovitis.

14 Claims, No Drawings

OTHER PUBLICATIONS

Okai et al, "Possible Immunomodulating Activities of Carotenoids in In Vitro Cell Culture Experiments", 1996, 753–758.

Turujman et al, "rapid Liquid chromatographic Method to Distinguish Wild Salmon from Aquacultured Salmon Fed Synthetic Astaxanthin", 1997, 622–632.

Nakagawa et al, "Inhibition by B–Carotene and Astaxanthin of NADPH–Dependent Microsomal Phospholipid Peroxidation", 1997, 345–355.

Kuschner, MD et al, "Endoscopic Versus Open Carpal Tunnel Release: Big Deal or Much Ado About Nothing?" Sep. 1997, 591–596.

Woodall et al, "Cartenoids and protection of phospholipids in solution or in liposomes against oxidation by peroxyl radicals: Relationship between carotenoid structure and protective ability", 1997, 575–586.

Chung, M.D., et al, "Endoxcopic versus Open Carpal Tunnel Release: A Cost–Effectiveness Analysis", 1997, 1089–1099.

Nieman, David, C., "Nutrition, Exercise and Immune System Function", 1999, 537–548.

Goldfarb, Allan, H., "Nutritional Antioxidants as Therapeutic and Preventive Modalities in Exercise–Induced Muscle Damage", 1999, 249–265.

METHOD OF RETARDING AND AMELIORATING CARPAL TUNNEL SYNDROME

FIELD OF THE INVENTION

This invention relates to the treatment and prevention of carpal tunnel syndrome. More particularly the invention relates to a method for treatment and prevention of carpal tunnel syndrome using, as a basis, the protective properties of astaxanthin. Most particularly the invention relates to treatment and prevention of carpal tunnel syndrome using orally administered astaxanthin.

BACKGROUND OF THE INVENTION

Carpal Tunnel Syndrome (CTS) is an ailment caused by excess pressure of the median nerve in the wrist resulting in numbness, tingling, and pain in the arm, hand, and fingers. Usually, CTS is considered a disorder caused by repetitive stress, physical injury, or other conditions that cause the tissues around the median nerve to become swollen. It occurs either when the protective lining of the tendons within the carpal tunnel becomes swollen or when the ligament that forms the roof becomes thicker and broader. Compression on the median nerve fibers by the swollen tendons and thickened ligament slows down the transmission of nerve signals through the carpal tunnel. The result is pain, numbness, and tingling in the wrist, hand and fingers except the little finger which is not affected by the median nerve.

The carpal tunnel is an opening into the hand that is made up of the bones of the wrist on the bottom and the transverse carpal ligament on the top. The tunnel is the space in the wrist bones where nine tendons for bending the hand and the median nerve pass from the forearm to the hand, the median nerve is relatively large, about the size of a pencil and contains thousands of small individual nerve fibers. The nerve also supplies a branch to the thenar muscle that allows the thumb to move, lift the thumb up and out from the hand and allow the thumb to turn and pinch the other fingertips (opposition). The other nerve fibers bring feeling from the tip of the thumb, index, middle, and part of the ring fingers.

The flexor tendons are important because they allow movement of the fingers and the hand for grasping objects. The tendons are covered by a material called tenosynovium. The tenosynovium is very slippery, and allows the tendons to glide against each other as the hand is used to grasp objects. Any condition that causes irritation or inflammation of the tendons can result in swelling and thickening of the tenosynovium. As the tenosynovium covering all of the tendons begin to swell and thicken, the pressure begins to increase in the carpal tunnel because the bones and ligaments that make up the tunnel are not able to stretch in response to the swelling. Increased pressure in the carpal tunnel begins to squeeze the median nerve against the transverse carpal ligament since the nerve is the softest structure in the carpal tunnel. Eventually, the pressure reaches a point when the nerve can no longer function normally and pain and numbness in the hand begins.

Pressure on the median nerve resulting from inflammation and a thickened lining of the tendons is called 'tenosynovitis'. When the pressure builds up, the blood flow in the nerve decreases and the nerve does not get enough oxygen. This results in the numbness and tingling feelings in the fingers. During sleep, the wrist is often bent down and pushes the nerve harder against the ligament. This further decreases the blood flow to the nerve and awakens people with the feeling that ones hand is "asleep." Tenosynovitis (swelling of the tendon sheath in the hands and fingers) is an associated repetitive stress injury of CTS and can effect various parts of the hand and fingers. One or more fingers may feel painful and stiff, especially in the morning; the wrist may be swollen. Trigger finger (also called snapping finger) is a condition brought on when a tendon thickens, leaving the finger in a bent position. It is a common complication of rheumatoid arthritis and may also occur in diabetes or for unknown causes. De Quervain's disease involves tenosynovitis at the base of the thumb. These disorders are often present with carpal tunnel syndrome.

The initial symptoms of carpal tunnel syndrome usually progress gradually over weeks and months and, in some cases, years. The first signs may be pain in the wrist and hand or numbness and tingling of the fingers, except the little finger. Patients may also experience a sense of weakness and a tendency to drop things. They may lose the sense of heat and cold or feel that their hands are swollen even though there is no visible swelling. The pain may also radiate up the arm to the shoulder, and, sometimes the neck. If the condition is allowed to progress, weakness of the thenar muscles can occur. This results in an inability to bring the thumb into opposition with the other fingers and hinders one's grasp. Symptoms may occur not only when the hand is being used but also when it is at rest. In fact, the disorder may be distinguished from similar conditions by pain occurring at night after going to bed. In some cases, labor-related CTS symptoms first occur outside of work, so patients may fail to associate the symptoms with work-related activity.

Repetitive work can cause pressure on the median nerve in locations other than the wrist and can also affect other nerves in the arm and hand. The branch of the median nerve that runs through the palm of the hand can be damaged directly by repeated pounding or by the use of certain tools requiring a strong grip using the palm, such as needle-nosed pliers. The median nerve can also be pinched up in the forearm. The ulnar nerve supplies sensation to the ring and little fingers. Like the median nerve, it too can become trapped as a result of repetitive stress, with subsequent loss of sensation in these fingers and the outer half of the palm. This condition, known as ulnar tunnel syndrome, can be a separate disorder or appear with carpal tunnel syndrome. In the latter case, release surgery for CTS usually also relieves the ulnar nerve entrapment. The ulnar nerve can also be affected at the elbow.

Evaluation begins by obtaining a history of the problem, followed by a thorough physical examination. Commonly, patients will complain first of waking in the middle of the night with pain and a feeling that the whole hand is asleep. Careful investigation usually shows that the little finger is unaffected. This can be a key piece of information to make the diagnosis. Other complaints include numbness while using the hand for gripping activities, such as sweeping, hammering, or driving. The major physical findings reflect that pressure is increased in the carpal tunnel. Several screens are available to see how well the median nerve is functioning, including the nerve conduction velocity test. This test measures how fast nerve impulses are conducted through the nerve.

In the early stages of carpal tunnel syndrome, a simple brace will sometimes decrease the symptoms, especially the numbness and pain occurring at night. Braces simply keep the wrist in a neutral position (not bent back too far nor bent down too far). When the wrist is in this position, the carpal tunnel is as large as it can be so the nerve has as much room as possible. The brace needs to be worn at night while one sleeps to prevent the numbness and pain occurring at night. If symptoms occur during the day as well, the brace may help reduce those symptoms as well. Standard conservative treatment for CTS is the splint plus anti-inflammatory medication, for several weeks.

Anti-inflammatory medicines are often recommended to help control the swelling of the tenosynovium and reduce the symptoms of carpal tunnel syndrome. These medications include the common over the counter medications such as ibuprofen and aspirin. In some studies, high doses of Vitamin B-6 have shown limited efficacy in decreasing the symptoms of CTS. Steroids are used to decrease inflammation and a local anesthetic is injected directly into the canal in an attempt to decrease the inflammation and swelling in the canal, thereby decreasing the compression on the median nerve and the patient's symptoms. This approach is often employed before surgery. It not only serves as a treatment option, it can be used as a diagnostic tool if the diagnosis is not certain. If the injection relieves the symptoms, CTS was most likely the correct diagnosis. If these simple measures fail to control CTS symptoms an injection of cortisone into the carpal tunnel may be necessary. This medication will decrease the swelling of the tenosynovium and may give temporary relief of symptoms. It is used not only to treat the problem, but serves to aid in diagnosis. If patients don't get at least temporary relief from the injection, it may be a sign that other problems exist that are causing the carpal tunnel symptoms. There is also a newer way to get cortisone medications down into the carpal tunnel. Iontophoresis is a technique where an electrical current is used to move the molecules of the medication through the skin down into the carpal tunnel. It is less painful than an injection, but is probably not as effective.

When medicines, changing activities, or splints prove to be ineffective in relieving symptoms, surgery may be required to reduce the pressure on the median nerve. Without surgery and continued pressure on the nerve, one loses feeling in the thumb, index, middle, and part of the ring finger. Without feeling heat, cold, or pain the fingers are more likely to be injured. Additionally, the thumb will lose the ability to lift out from the palm of the hand, because some thumb muscles become paralyzed. Prolonged damage may become permanent. Carpal tunnel syndrome can range from a minor inconvenience to a disabling condition, depending on its cause and persistence and the individual characteristics of the patient. Proper treatment of other medical conditions that cause carpal tunnel syndrome can often help reduce wrist swelling. If severe cases are left untreated, however, muscles at the base of the thumb may atrophy and sensation may be permanently lost. CTS can become so crippling that people can no longer do their job or even perform simple tasks at home.

There are several different surgical procedures designed to relieve pressure on the median nerve. The most common are the traditional 'open carpal tunnel release' and the newer 'endoscopic carpal tunnel release' which use a smaller incision and a fiberoptic TV camera to help see inside the carpal tunnel. The operation consists of cutting the ligament that forms the roof of the tunnel. Releasing the ligament relieves the pressure on the nerve. Additional procedures may be necessary. Sometimes swollen tissue or other structures in the tunnel that are pressing on the nerve need to be removed. When the nerve has been compressed for a long time, scar tissue builds inside the nerve. When this happens, usually the fingers remain numb all the time and you lose delicate sensation. The muscles that lift the thumb out from the hand may also have become partly paralyzed. With excessive scar tissue, an internal neurolysis is added to the operation of ligament release. In this procedure, using magnification, the outer wrapping of the nerve is opened and the scar tissue is removed from within the nerve.

In 1988, 2.8 million people reported symptoms to their doctors believed to be those of carpal tunnel syndrome. In a 1998 British study, experts estimated that between 7% and 16% of the population experience CTS. The incidence appears to be increasing and it appears that people over age 54 are at higher risk than younger adults. Disorders related to work that requires repetitive motions are increasing and now account for nearly half of all reported work-related illness. Carpal tunnel syndrome is estimated to account for over 41% of these repetitive motion disorders. Researchers have defined six key risk factors in the workplace for the development of CTS as: 1) repetition; 2) high force; 3) awkward joint posture; 4) direct pressure; 5) vibration; and 6) prolonged constrained posture. Some experts believe that incorrect posture may play a large role in the development of CTS, particularly in people who work at computer and other types of keyboards. The tendency to roll the shoulders forward, round the lower back, and thrust the chin forward can shorten the neck and shoulder muscles, compressing nerves in the neck. This, in turn, can affect the wrist, fingers, and hand.

Occupation-related causes of CTS have had a severe impact on American businesses. Workers with CTS become easily fatigued, experience pain and discomfort, and may not perform up to par. Employers are concerned about high worker's compensation costs due to CTS, which may or may not be due to working conditions. The medical costs and loss of productivity because of carpal tunnel syndrome has been estimated to average $29,000 per injured worker. Work-related injuries, including carpal tunnel syndrome, that involve joints and muscles cost the country about $20 billion every year. At high risk are those whose occupations combine force and repetition of the same motion in the fingers and hand for long periods. Such workers include those in the meat and fish packing industries and workers using vibrating tools, like jack hammers or chain saws. Meat packers complained of pain and loss of hand function as long ago as the 1860's. Today, the incidence of carpal tunnel syndrome in meat, poultry, and fish packing industries may be as high as 15%. In addition, high risk for CTS has been reported in other assembly line workers such as food and beverage processing, cake decorators, postal workers, dentists, and dental technicians, virtually any workers who use their hands and wrists repetitively.

Algae

Although natural sources of astaxanthin are numerous, nearly all are found in very low concentrations. Astaxanthin is quite common in nature, especially in the marine environment and is probably best known for eliciting the pinkish-red hue to the flesh of salmon and trout, as well as shrimp, lobsters and crayfish. These animals obtain astaxanthin in their diet from zooplankton, insects or crustaceans that have accumulated astaxanthin from phytoplankton.

The green algae *Haematococcus pluvialis* provides the most concentrated natural source of astaxanthin known, from 10,000–40,000 ppm (mg/kg) astaxanthin in addition to other important carotenoids such as beta-carotene, lutein and canthaxanthin. Whereas, the flesh of wild Atlantic salmon contain approximately 5 ppm of astaxanthin, Coho salmon about 14 ppm astaxanthin and sockeye salmon average 40 ppm (Turujman, 1997). Other sources of astaxanthin include processed crustacean wastes from krill, shrimp, crab and crawfish, the fermentative yeast *Phaffia rhodozyma* and chemically synthesized astaxanthin. *Haematococcus pluvialis,* also referred to as *Haematococcus lacustris* or *Sphaerella lacustris,* is a ubiquitous green alga of the order Volvocales, family Haematococcaceae. It is now known that the alga occurs in nature worldwide, where environmental conditions for its growth are favorable. Haematococcus occurs in nature worldwide, but is most often found in cooler pools of fresh water such as garden birdbaths. Under nutrient-rich conditions, Haematococcus is motile and utilizes the available nitrate, phosphate, and other nutrients to grow and reproduce. However, when nutrients become limiting or the pool begins to dry the alga form a protective cell wall and encyst. High concentrations of astaxanthin are produced, and the cells undergo a dormant stage until the next influx of water and nutrients. Cells can remain viable in this encysted stage with its protective astaxanthin for many years. Red cysts are significantly more resistant to strong light and oxygen radicals than green cells, suggesting significant protective roles for astaxanthin (Kobayashi et al., 1992a).

Astaxanthin, is biosynthesized through the isoprenoid pathway, which initiates at acetyl-Co-A and proceeds through phytoene, lycopene, β-carotene, and canthaxanthin before the last oxidative steps to astaxanthin. Fatty acids are esterified onto the 3' hydroxyl group(s) of astaxanthin after biosynthesis of the carotenoid, and allow it to have more solubility and stability in the cellular environment. The fatty acids that are esterified to astaxanthin are those found typically in the Haematococcus cells. Grung et al. (1992) compared the carotenoids in three strains of Haematococcus. More than 80% of the carotenoids in all strains was astaxanthin esterified to C16:0 (palmitic) and C18:1 (oleic) fatty sacids. (Grung M., F. M. L. D'Souza, M. Borowitzka, and S. Liaen-Jensen. 1992. Algal carotenoids 51, secondary carotenoids 2. *Haematococcus pluvialis* aplanospores as a source of (3S, 3'S)-astaxanthin esters. J. Appl. Phycol. 4:165–171.). Another group found the monoester group makes up the majority of the total astaxanthin in Haematococcus. C18:1 (oleic) and C18:2 (linoleic) are the main unsaturated fatty acids, whereas C16:0 (palmitic), C18:0 (stearic) predominate as the saturated fatty acids that are esterfied. (Renstrom, B. and S. Liaaen-Jensen. 1981. Fatty acid compostion of some esterified carotenols. Comp. Biochen. Physiol. B., 69: 625–627.). The carotenoid fraction of green vegetative cells consists of mostly lutein (75–80%) and β-carotene (10–20%). Whereas in red cysts, the predominate carotenoid is astaxanthin (Renstrom et al., 1981). Free astaxanthin and its mono- and diesters from Haematococcus have optically pure (3S,3'S)-chirality (Grung et al., 1992 and Renstrom et al., 1981).

Advanced technology has been developed to grow Haematococcus in closed culture systems and harnesses the unique properties of the algae to produce very high concentrations of natural astaxanthin. Lots are generally standardized to contain 1.5% (15,000 ppm) astaxanthin. Other beneficial carotenoids such as β-carotene, canthaxanthin, and lutein are also present in lesser amounts. The astaxanthin is predominately in the esterified form which provides the highest stability. Most importantly, the production process includes a technique which 'cracks' greater than 95% of the cells to enable maximum bioavailability, resulting in a fine dark red powder.

Dried Haematococcus algae, Phaffia yeast powder, or synthetic astaxanthin can be formulated into various food grade oils such as safflower, canola, tocopherols or rice bran and manufactured into gelcaps for convenient ingestion. Alternatively, dried Haematococcus algae, Phaffia yeast powder, or synthetic astaxanthin can be stabilized by various commercial processes and added directly to foods or beverages.

Prior Research

Researchers have developed a variety of methods to measure the antioxidant capacity of carotenoids. Some of these assays are conducted in test tubes (in vitro) to better control conditions or within cells themselves (in vivo). Typically, a chemical that generates free radicals or peroxides is mixed with a substrate such as a fatty acid that can become readily oxidized. When the reaction rate is determined, carotenoids or other antioxidants can then be added to determine how it quenches, or slows the peroxidation rate of the fatty acid. Numerous studies exist demonstrating the potent radical scavenging and singlet oxygen quenching properties of astaxanthin (Haila, 1997;Woodall, 1997;Nakagawa, 1997;Oshima, 1993; Tinkler, 1994). It has been demonstrated that astaxanthin is significantly more effective in neutralizing free radicals than beta-carotene and protects against peroxidation of unsaturated fatty acid methyl esters better than canthaxanthin, beta-carotene or zeaxanthin (Terao, 1989; Jorgensen, 1993).

The unique structure of astaxanthin scavenges lipid radicals and effectively breaks peroxide chain reactions (Terao, 1989). Di Mascio utilized a chemiluminescent technique to express the superior singlet oxygen quenching ability of astaxanthin compared to other carotenoids. He also concluded that the effectiveness and potency of astaxanthin was even better expressed at the lower oxygen concentrations found in tissues, as opposed to higher oxygen concentrations normally used with in vitro conditions (Di Mascio, 1989). Many antioxidant studies are conducted under conditions of low vitamin E (tocopherol) or vitamin A to better assess the actual effects of the added carotenoids. In vitamin E-deficient rats, astaxanthin protects the mitochondria from damage caused by lipid peroxidation.

The antioxidant activity of astaxanthin is much greater than vitamin E (Kurashige, 1990). A number of studies have shown that astaxanthin has an activity 80–550 times greater than alpha-tocopherol, also known as vitamin E (Di Mascio, 1989; Ranby and Rabek 1978; Shimidzu, 1996). One prominent researcher has proposed astaxanthin as the 'super vitamin E' (Miki, 1991). Although researchers use different assay systems, the antioxidant activity of astaxanthin has been shown to be approximately 10 times stronger than the antioxidant activity of other carotenoids such as zeaxanthin, lutein, beta-carotene and canthaxanthin (Miki, 1991).

Enzymatic and non-enzymatic antioxidant systems play a vital role in protecting tissues from excessive oxidative damage during exercise. Depletion of each of the antioxidant systems increases the vulnerability of various tissues and cellular components to reactive oxygen species (Ji, 1995). There is consistent evidence from human and animal studies that strenuous physical exercise may induce a state wherein the antioxidant defenses of several tissues are overwhelmed by excess reactive oxygen (Sen, 1995). Physical exercise causes oxidative stress that leads to the formation of reactive oxygen and nitrogen species (Poulsen, 1998; Caillaud, 1999). This may lead to DNA and muscle tissue damage. Exercise induced oxidative stress has also been shown to reduce the concentration of vitamin A and coenzyme Q (Quiles, 1999). Free radicals formed during oxidative stress have been shown to play an important role as mediators of skeletal muscle damage and inflammation after strenuous exercise (Dekkers, 1996). Free radical formation has been linked to lipid peroxidation (Witt, 1992) and protein damage (Radak, 1999) as well as demonstrated to be a contributing factor in the loss of calcium homeostasis within cells (Goldfarb, 1999).

Free radicals generated by oxidative stress from exercise have been shown to change immune function and lead to an inflammatory response (Niess, 1999). Many components of the immune system exhibit adverse change after prolonged, intense exertion. A period of impaired immunity may last from 3 to 72 hours depending on the immune measure (Nieman, 1999). Prolonged stress as a result of excessive exercise can lead to a decline in certain aspects of immune system function such as natural killer cell cytotoxicity or secretory-IgA (Kelly, 1999)

Many researchers recommend the consumption of antioxidant compounds to counteract the oxidative damage that occurs during exercise. Human studies have shown that dietary supplementation with antioxidant vitamins such as vitamin E and C have a favorable effect on lipid peroxidation after exercise (Derkkers, 1996; Goldfarb, 1993; Kanter, 1998). Beta-carotene and antioxidant coenzyme Q10 have been suggested as dietary supplements to minimize the oxidative damage during exercise (Witt, 1992). Selenium dietary supplements have also been shown to reduce free radical formation during exercise in rats (Konda, 1998).

Epidemiological studies have demonstrated a correlation between increased carotenoid intake and the reduced incidence of coronary heart disease and certain cancers, macular degeneration, and increased resistance to viral, bacterial, fungal and parasitic infections (Seddon, 1994; Zhang, 1999, Rao, 1999; Rumi, 1999; Batieha, 1993). Studies indicate that the mechanism for this protective attribute is partly due to the direct enhancement of the immune response by carotenoids. Anticarcinogenic effects of carotenoids are likely attributable to its antioxidant effect, insofar as oxygen radicals are related to the process of cancer initiation and propagation.

Singlet oxygen is also cytotoxic to the immune system by virtue of its ability to catalyze production of free radicals. This action can facilitate degradation of macrophage cell membranes resulting in dysfunction and reduced efficiency of phagocytosis (Bendich, 1991). Carotenoids have been shown to enhance both the non-specific and specific immune system and protect cell membranes and cellular DNA from mutation (Bendich A. 1989). Carotenoids have a significant stimulatory effect on the immune system, as seen by the proliferative response of spleen cells and thymocytes during antibody response of mice. Astaxanthin enhances the release of interleukin-1 alpha and tumor necrosis factor alpha in mice to a greater degree than canthaxanthin and beta-carotene. The conclusion of one study was that astaxanthin had the best cytokine-inducing activity and may provide an immunomodulating role (Okai, 1996).

In one series of immune system challenges, astaxanthin enhanced T-helper cell antibody production even when suboptimal amounts of antigen were present. Furthermore, astaxanthin, but not other carotenoids (canthaxanthin, beta-carotene, lutein, lycopene), increased the number of antibody-secreting cells from primed spleen cells (Jyonouchi, 1996). Using human blood, it was shown that astaxanthin enhances the production of IgM, IgA and IgG antibodies in response to T-dependent stimuli (Jyonouchi, 1995a and 1995b). Another study indicates a significant immunomodulating action of astaxanthin for humoral immune responses to T-dependent antigens and the authors suggest that carotenoid supplementation may be beneficial in restoring humoral immune responses in older animals. Furthermore, it was speculated that dietary carotenoids could reduce the chance of developing autoimmunity and malignancies by enhancing T-helper functions and promoting specific antibody responses (Jyonouchi, 1994).

Monocytes are a particular type of white blood cell which contain surface proteins that distinguish cancer cells from normal healthy ones. When these MHC II proteins identify cancer cells they signal the immune system to attack them. Monocytes do not identify cancer cells if the monocytes don't have enough MHC II proteins. It was demonstrated that supplementation with a carotenoid in the diet increases the number of MHC II proteins on monocytes. In turn, subjects had increased production of tumor necrosis factor alpha (TNF-a) which helps kills cancerous and virus-infected cells (Hughs, 1997).

Supplementation with carotenoids increases the number of circulating lymphocytes (T-helper cells), enhances T and B lymphocyte proliferation, improves rejection of foreign tissue, increases killer cell destruction of tumor cells and neutrophil killing of Candida fungi, and inhibits loss of macrophage receptors (Bendich, 1990). Mice fed carotenoids had significantly reduced tumor growth when the primary lesion was excised and then re-challenged with the same tumor (Tomita, 1987). Virus-induced tumors such as murine sarcoma are slowed by carotenoids, as well as adenocarcinoma, squamous cell carcinoma, fibrosarcoma, and chemically induced tumors (Bendich, 1990). These studies present strong evidence that orally administered astaxanthin and other carotenoids can directly affect the immune responses to foreign antigens and cancerous tumors.

Even with all the research to date, there still does not exist very effective, non-invasive treatments for retarding and ameliorating carpal tunnel syndrome and tenosynovitis. Surgery remains the last resort and sometimes only option for effective treatment. Thus there remains a need for an effective, less invasive or non-invasive treatment of these conditions.

SUMMARY OF THE INVENTION

Astaxanthin is a potent antioxidant, over 500 times more powerful than Vitamin E and 10 times stronger than other carotenoids such as zeaxanthin, lutein, canthaxanthin and betacarotene. Astaxanthin has also been shown to enhance and modulate the immune system. These effects in combination or separately are able to retard and ameliorate carpal tunnel syndrome when astaxanthin is ingested or delivered by iontophoresis in a therapeutically effective dose.

Thus one aspect of the invention is to produce an inexpensive means to retard and ameliorate carpal tunnel syndrome.

Another aspect of the invention is to provide a means to retard and ameliorate carpal tunnel syndrome that is ingestible.

Yet another aspect of the invention is to provide a means to retard and ameliorate carpal tunnel syndrome that is deliverable to the affected area by iontophoresis.

Another aspect of the invention is to use the unique antioxidant and immune modulation properties of astaxanthin to retard and ameliorate carpal tunnel syndrome.

A still further aspect of the invention is to provide a therapeutically effective dose of ingestible astaxanthin in the range of about 1–100 mg per day to retard and ameliorate carpal tunnel syndrome.

These and further aspects of the invention will be shown as illustrated in the following detailed description of the invention, and the appended claims.

DETAILED DESCRIPTION OF THE INVENTION

Astaxanthin is a potent antioxidant with over 10 times the antioxidant activity of other carotenoids such as zeaxanthin, lutein, beta-carotene and canthaxanthin and up to 500 times the antioxidant activity of vitamin E. Further, research has shown that astaxanthin enhances the immune system. As described above, astaxanthin is biosynthesized through the isoprenoid pathway which initiates at acetyl-Co-A and proceeds through phytoene, lycopene, beta-carotene, and canthaxanthin before the last oxidative steps to astaxanthin. Fatty acids are esterified onto the 3' hydroxyl group(s) of astaxathin after biosynthesis of the carotenoid, and allow it to have more solubility and stability in the cellular environment. The fatty acids that are esterified to astaxanthin are those found typically in the Haematococcus cells. More than 80% of the carotenoids in all strains was astaxanthin esterified to C16:0 (palmitic) and C18:1 (oleic) fatty acids. Phaffia yeast produces non-esterified astaxanthin. Synthetic astaxanthin, or astaxanthin from Phaffia yeast, could be used as the free form of astaxanthin or esterified with various fatty acids, such as those found in Haematococcus cells.

Applicant's technology produces very high concentrations of natural astaxanthin. Lots are generally standardized to contain 1.5% (15,000 ppm) astaxanthin, predominantly in the esterified form which provides the greatest stability.

Free radicals generated by oxidative stress from repetitive movement and exercise have been shown to change immune function, and lead to lipid peroxidation and an inflammatory response. Human studies have shown that dietary supplementation with antioxidant vitamins such as vitamin E and C have a favorable effect on lipid peroxidation after exercise. Thus, many researchers recommend the consumption of antioxidant compounds to counteract the oxidative damage that occurs during exercise.

With respect to CTS and tenosynovitis, it is known that these conditions can result from the stress of repeated exercise to the arm and hand which leads to inflammation and swelling. Anti-inflammatory medicines are often recommended to help control the swelling of the tenosynovium and reduce the symptoms of CTS. These medications include the common over the counter medications such as ibuprofen and aspirin as well as injections of steroids or cortisone.

Since astaxanthin is a potent antioxidant and can also enhance the immune system, Applicants realized that astaxanthin could be effectively used to counteract oxidative stress and inflammation which leads to CTS.

It has been noted that the algae Haematococcus is an excellent source of natural astaxanthin. Advanced technology has been developed to grow Haematococcus in closed culture systems and harnesses the unique properties of the algae to produce very high concentrations of natural astaxanthin.

Dried Haematococcus algae, Phaffia yeast powder, or synthetic astaxanthin can be formulated into various food grade oils such as safflower, canola, tocopherols or rice bran and manufactured into gelcaps for convenient ingestion. Alternatively, dried Haematococcus algae, Phaffia yeast powder, or synthetic astaxanthin can be stabilized by various commercial processes and added directly to foods or beverages.

The carotenoid astaxanthin has never been suggested as a dietary supplement to retard or ameliorate carpal tunnel syndrome. Nor have the combined properties of astaxanthin as a potent antioxidant and an immune system modulator been previously recognized as a dietary supplement to retard or ameliorate carpal tunnel syndrome. Thus, Applicants present a novel treatment and method for retarding and ameliorating CTS.

The invention is a treatment and method of retarding and ameliorating CTS by administering a therapeutically effective dose of astaxanthin.

The astaxanthin is preferably administered orally, in doses of between about 1 to about 100 mg per day. Doses of between about 2 to about 10 mg per day are preferable. The dose may be administered to be taken with meals, twice daily.

In addition to an oral administration, a formulation of astaxanthin may also be injected into the affected area, or applied by the iontophoresis technique described above. Such a dose would also be in the range of about 1 to 100 mg per day.

EXAMPLE 1

Haematococcus algae meal containing 1.5% astaxanthin was thoroughly mixed with safflower oil such that the resulting suspension contained 2.0 mg of pure astaxanthin per gram of safflower oil suspension. 500 mg soft gel capsules were produced from the safflower oil suspension such that each soft gel capsule contained 1.0 mg of pure astaxanthin.

One individual was a 51 year-old male who has suffered from wrist pain, numbness and tingling for two years due to continued keyboard use on a computer for 40 hours per week. One doctor diagnosed the affliction in his right wrist as carpal tunnel syndrome/tenosynovitis and prescribed an anti-inflammatory drug and gamma-linolenic acid supplement. His grip in the afflicted wrist was only 60% of his non-afflicted wrist. The drug and supplement were not effective after 30 days so the treatment was abandoned. The patient was also given a wrist brace to be used at work and while sleeping. The tingling and numbness continued for the next two years and he went to another doctor for treatment. A second doctor also diagnosed carpal tunnel syndrome and prescribed another anti-inflammatory drug, but it was ineffective after 30 days and abandoned. The doctor referred him to a surgeon who also diagnosed the condition as carpal tunnel syndrome and explained operative procedures.

Soon thereafter, the individual began taking 6 milligrams of astaxanthin per day derived from Haematococcus algae. This was ingested, using the oil-suspension gelcaps described above, with 3 milligrams of astaxanthin consumed with lunch and 3 milligrams with dinner. After 1 week of ingesting the astaxanthin, the individual noticed a significant lessening of the pain and tingling but continued to wear the wrist brace. After two weeks of astaxanthin supplementation, the tingling and numbness was nearly alleviated and he was able to eliminate the wrist brace during sleep and at work without tingling and pain. Over the next two weeks the symptoms were completely mitigated. After three months of supplementation with astaxanthin, the patient continues normal activities without symptoms of carpal tunnel syndrome or tenosynovitis.

EXAMPLE 2

A 42 year-old female was diagnosed with carpal tunnel syndrome for seven months and wore a wrist brace to alleviate pain while working as a secretary and performing normal home activities. She awoke at least once during the night with numbness and tingling in her wrist.

The individual began taking 6 milligrams of astaxanthin per day derived from Haematococcus algae (as described in the above example 1). Three milligrams of astaxanthin were consumed with lunch and 3 milligrams with dinner. After 2 weeks of ingesting the astaxanthin the individual was not awakened at night with numbness and tingling in the wrist. After three weeks of astaxanthin supplementation, pain and discomfort during the daytime was alleviated and she no longer required a wrist brace at work or home.

While the above description and examples disclose some preferred embodiments of the invention, there may be variations that, while not specifically described, do not depart from the spirit and scope of the invention as described above and in the appended claims.

What is claimed is:

1. A method to retard and ameliorate carpal tunnel syndrome comprising administering a therapeutically effective dose of astaxanthin to a patient in need thereof.

2. The method according to claim 1 wherein said therapeutically effective dose is in the range of about 1 to 100 mg of astaxanthin per day.

3. The method according to claim 1 wherein said astaxanthin is in a form esterified with fatty acids.

4. The method according to claim 1 wherein said astaxanthin is derived from natural sources.

5. The method according to claim 4 wherein said natural sources are Haematococcus algae, or Phaffia yeast powder.

6. The method according to claim 1 wherein said astaxanthin is produced synthetically.

7. The method according to claim 2 wherein said therapeutically effective dose is in the range of about 2 to 10 mg of astaxanthin per day.

8. The method according to claim 1 wherein said therapeutically effective dose is administered orally to the patient.

9. The method according to claim 8 wherein said therapeutically effective dose is achieved by administering said astaxanthin twice daily, in two equal doses.

10. A method to retard and ameliorate carpal tunnel syndrome comprising administering, to a patient in need thereof, a therapeutically effective dose of astaxanthin to the affected area by iontophoresis.

11. The method according to claim 10 wherein said therapeutically effective dose is in the range of about 1 to 100 mg of astaxanthin per day.

12. The method according to claim 11 wherein said therapeutically effective dose is in the range of about 2 to 10 mg of astaxanthin per day.

13. A method of treating and ameliorating carpal tunnel syndrome comprising a therapeutically effective dose, in the range of about 1–100 mg per day, of astaxanthin administered to a patient, in need thereof, orally, or delivered to the affected area by iontophoresis.

14. The method of treating according to claim 13 comprising about 2–10 mg of staxanthin per day.

* * * * *